United States Patent [19]

Franz et al.

[11] Patent Number: 5,399,795
[45] Date of Patent: Mar. 21, 1995

[54] PROCESS FOR THE PREPARATION OF 2-H-HEPTAFLUOROPROPANE

[75] Inventors: Raimund Franz, Kelkheim; Günter Siegemund, Hofheim, both of Germany

[73] Assignee: Hoechst Aktiengesellschaft, Frankfurt, Germany

[21] Appl. No.: 273,945

[22] Filed: Jul. 12, 1994

[30] Foreign Application Priority Data

Jul. 14, 1993 [DE] Germany .................. 43 23 054.7

[51] Int. Cl.⁶ ............................................ C07C 17/08
[52] U.S. Cl. .................................................... 570/165
[58] Field of Search ........................................ 570/165

[56] References Cited

U.S. PATENT DOCUMENTS 4,766,258  8/1988  Komatsu et al. ............... 570/165
5,268,343 12/1993  Hopp et al. ................... 570/165

FOREIGN PATENT DOCUMENTS 0902590  8/1962  United Kingdom .
0905617  9/1962  United Kingdom .

OTHER PUBLICATIONS

Miller Jr., W. T., et al, *JACS* 82:3091–3099 (1960).

*Primary Examiner*—Alan Siegel
*Attorney, Agent, or Firm*—Connolly & Hutz

[57] ABSTRACT

The invention relates to a process for the preparation of 2-H-heptafluoropropane, wherein hexafluoropropene is reacted with hydrogen fluoride in the presence of a weakly basic ion exchanger whose reactive centers comprise tertiary amino groups.

5 Claims, No Drawings

PROCESS FOR THE PREPARATION OF 2-H-HEPTAFLUOROPROPANE

The invention relates to a novel process for the preparation of 2-H-heptafluoropropane. 2-H-Heptafluoropropane (R 227) is a fluorocarbon boiling at ca. −18° C. which is chlorine-free and hence harmless to the stratospheric ozone layer; it is of increasing industrial importance, e.g. as a propellant. A few other methods of production have been disclosed since it was first prepared in 1946 by the hydrolysis of a Grignard compound. Processes which are suitable for an industrial-scale reaction are predominantly those which involve the direct or indirect addition of hydrogen fluoride onto hexafluoropropene:

$$CF_3-CF=CF_2+HF \rightarrow CF_3-CHF-CF_3$$

The oldest method of this type is the reaction of hexafluoropropene with potassium fluoride in formamide published by W. T. Miller et al. (JACS 82, 3091–3099 (1960)):

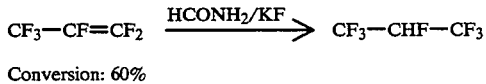

$$CF_3-CF=CF_2 \xrightarrow{HCONH_2/KF} CF_3-CHF-CF_3$$

Conversion: 60%

A crucial disadvantage of this process is that the hydrogen atom required for this indirect addition of HF is abstracted from the reaction medium (i.e. the formamide) by cleavage, leading to the formation of undesired by-products. Subsequently, attempts were therefore made to effect the addition by the direct action of hydrogen fluoride on hexafluoropropene, conveniently in the presence of a catalyst. However, these attempts have so far only been successful when using high reaction temperatures. In a process described in British patent 902 590, an equimolar gaseous mixture of hexafluoropropene and hydrogen fluoride, flowing through a tubular reactor packed with activated charcoal, is only converted to 2-H-heptafluoropropane at temperatures between 250° and 450° C.

Working with gaseous mixtures at such high temperatures is always associated with problems of a technical and chemical nature. Rigorous demands are made on the operating safety and on the corrosion resistance of the materials involved; it is moreover known that fluorocarbons above 250° C. can be expected to undergo increasing thermal degradation, the extent of which becomes considerable above 500° C. According to British patent 905 617, in the same apparatus as that required for the preparation of 2-H-heptafluoropropane, the 2-H-heptafluoropropane undergoes a thermal reaction at 545° C. to give perfluoropropane (17% of theory) and 2-H-nonafluoroisobutane (27% of theory). Thus traces of these products can already be expected to appear in the temperature range mentioned above for the preparation of 2-H-heptafluoropropane. It should be pointed out here that the highly toxic perfluoroisobutene can easily be formed from 2-H-nonafluoroisobutane at elevated temperature.

It has now been found, surprisingly, that hexafluoropropens and hydrogen fluoride react together extremely readily, in an addition reaction, when a weakly basic ion exchanger whose reactive centers comprise tertiary amino groups is used as a solid catalyst. Rather than requiring the application of heat, the reaction is exothermic.

The present invention thus relates to a process for the preparation of 2-H-heptafluoropropane from hexafluoropropens, wherein hexafluoropropene is reacted with hydrogen fluoride in the presence of a weakly basic ion exchanger whose reactive centers comprise tertiary amino groups.

Apparatuses which can be used for the reaction according to the invention are closed pressure vessels into which the reactants are pumped; it is also possible, however, to adopt a pressureless continuous reaction procedure, for which simple tubular reactors or else fluidized-bed reactors are particularly suitable. The reactor to be used here is conveniently made of a material which is resistant to hydrogen fluoride (e.g. stainless steel, nickel, ®Hastelloy or plastic).

Commercially available materials, such as those used for water conditioning or comparable purposes, can be employed as weakly basic ion exchangers whose reactive centers comprise tertiary amino groups, an example being the product ®Amberlite IRA 93 SP from Rohm & Haas. The ion exchanger is introduced into the reactor as a free-flowing charge or as a suspension in a high-boiling inert liquid such as paraffin oil. Any water present is conveniently removed beforehand, provided this can be done without great expense, e.g. by drying to constant weight at a slightly elevated temperature under vacuum.

Depending on the design of the apparatus, it can be advantageous to moderate the strongly exothermic reaction by precharging the ion exchanger to be used with hydrogen fluoride. This precharging can take place in the reaction apparatus itself or else externally and should amount to at most 33 g, preferably 8–25 g and especially 18–23 g of hydrogen fluoride per 100 g of ion exchanger.

The reactants of the reaction according to the invention, i.e. hexafluoropropene and hydrogen fluoride, are conveniently introduced simultaneously in gaseous form into the reactor, containing the chosen ion exchanger, in a molar ratio of 0.9–1.1:1, preferably 1:1, i.e. in a weight ratio of 7.5:1. The 2-H-heptafluoropropane is generally isolated by simply condensing the gas obtained on depressurizing the pressure vessel used or as the product of a continuously operating apparatus. It may be necessary, however, to remove entrained traces of hydrogen fluoride or amines from the crude product by means of alkaline or acid scrubbing processes. Working-up by distillation may also be necessary if a high degree of purity is required.

The temperatures for the reaction according to the invention depend essentially on the heat stability of the ion exchanger used. They are generally 20°–120° C., preferably 30°–90° C. and especially 50°–70° C.

The following Examples will serve to illustrate the process according to the invention.

EXAMPLE 1

120 g of the ion exchanger ®Amberlite type IRA 93 SP (Rohm & Haas) (previously dried to constant weight at 80° C. under vacuum) were treated with 14 g of gaseous hydrogen fluoride in a closed plastic vessel, with shaking, the hydrogen fluoride being uniformly and completely absorbed. The reactor used was a vertical stainless steel tube of length 60 cm and internal diameter 3 cm, jacketed for external cooling. The tube was provided with a fine-meshed perforated bottom. A thin, centrally mounted metal tube, closed at the bottom end, served to accommodate thermocouples. The reactor was packed with the ion exchanger precharged with HF, closed and connected to a gas-sampling device and a cold trap. Hexafluoropropene was then passed in underneath the perforated bottom at a rate of 180 mmol/h and, when the reaction had started (recognizable by the temperature rise at the foot of the tube), hydrogen fluoride was metered in, also at a rate of 180 mmol/h, the internal temperature rising to ca. 60° C.; at this temperature the heat of reaction was dissipated by the circulation of cooling water at 23° C. The first gas sample was taken 50 minutes after the start of the reaction and all further samples were taken at half-hour intervals. The content of 2-H-heptafluoropropane in the crude gas mixture reached 94.6% (GC conditions: 5 m ®Porasil-C column, 5% OPN (oxydipropionitrile), isothermal at 80° C., thermal conductivity detector).

EXAMPLE 2

15 g of ®Amberlite IRA 93 SP, precharged with 2.8 g of hydrogen fluoride, were placed in a ®Hastelloy-C stirred autoclave of capacity 300 ml and suspended in 100 g of a perfluorinated polyether boiling at 216° C. After the autoclave had been closed, 14 g of hexafluoropropene were introduced under pressure and the mixture was stirred for 6.5 h at 50° C. under autogenous pressure. The gas chromatogram (conditions as in Example 1) of a sample taken thereafter showed a 2-H-heptafluoropropane content of 85.5% and a hexafluoropropene content of ca. 14.1% in the crude product.

We claim:

1. A process for the preparation of 2-H-heptafluoropropane from hexafluoropropene, wherein hexafluoropropene is reacted with hydrogen fluoride in the presence of a weakly basic ion exchanger whose reactive centers comprise tertiary amino groups.

2. The process as claimed in claim 1, wherein hexafluoropropene and HF are used in a molar ratio of 0.9:1 to 1.1:1.

3. The process as claimed in claim 1, wherein the reaction is carried out at a temperature of 20° to 120° C.

4. The process as claimed in claim 1, wherein the reaction is carried out at a temperature of 30° to 90° C.

5. The process as claimed in claim 1, wherein the reaction is carried out at a temperature of 50° to 70° C.

* * * * *